United States Patent [19]
Chang

[11] Patent Number: 5,442,298
[45] Date of Patent: Aug. 15, 1995

[54] METHOD AND APPARATUS FOR MEASURING RESISTIVITY OF GEOMETRICALLY UNDEFINED MATERIALS

[76] Inventor: On-Kok Chang, 1031 Belvedere La., San Jose, Calif. 95129

[21] Appl. No.: 40,054

[22] Filed: Mar. 30, 1993

[51] Int. Cl.⁶ ............................................. G01N 27/04
[52] U.S. Cl. ..................................... 324/724; 324/713; 324/722
[58] Field of Search ............... 324/691, 693, 713, 715, 324/722, 724, 757

[56] References Cited

U.S. PATENT DOCUMENTS

| | | | |
|---|---|---|---|
| 2,082,364 | 6/1937 | Store | 324/724 X |
| 2,370,658 | 3/1945 | Hart | 324/724 X |
| 3,005,152 | 10/1961 | Jennings et al. | 324/724 X |
| 3,005,153 | 10/1961 | Berkley et al. | 324/724 X |
| 4,646,000 | 2/1987 | Wills | 324/693 X |
| 4,876,904 | 10/1989 | Limon | 324/693 X |
| 4,954,783 | 9/1990 | Spry | 324/724 X |
| 4,976,549 | 12/1990 | Khan | 324/713 X |

Primary Examiner—Kenneth A. Wieber
Assistant Examiner—Glenn W. Brown
Attorney, Agent, or Firm—Patrick Keane

[57] ABSTRACT

The present invention relates to an apparatus and method for measuring electrical characteristics of materials having undefined geometries in an accurate and reproducible manner. Generally speaking, electrical characteristics such as conductivity and resistance are measured by compressing the material with a predetermined force or pressure in a controlled manner to provide reproducible results.

28 Claims, 2 Drawing Sheets

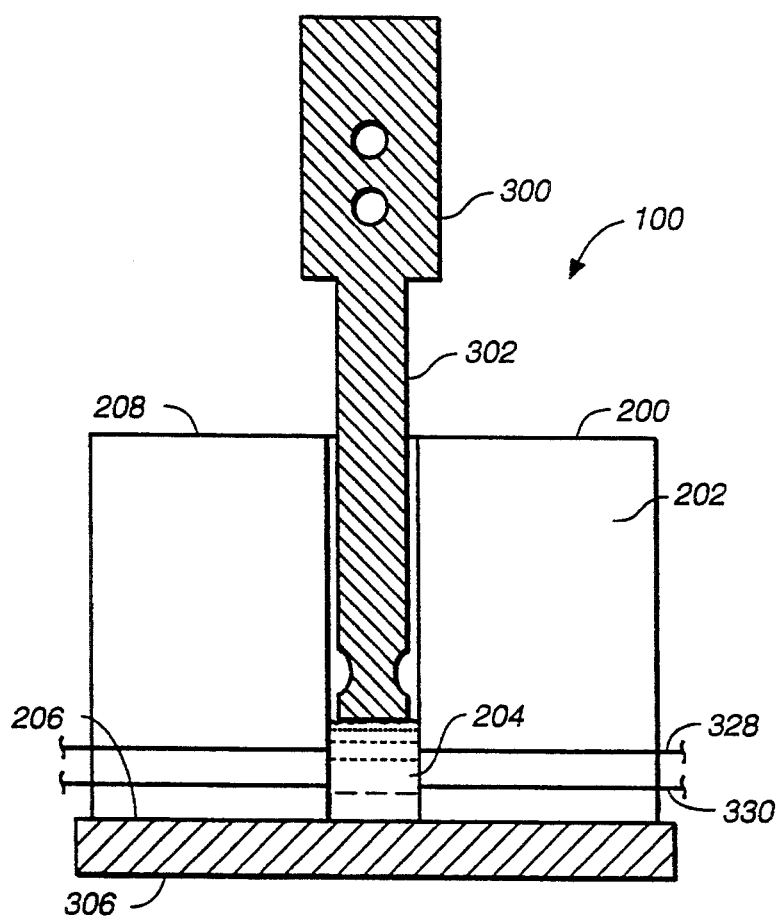
FIG._1
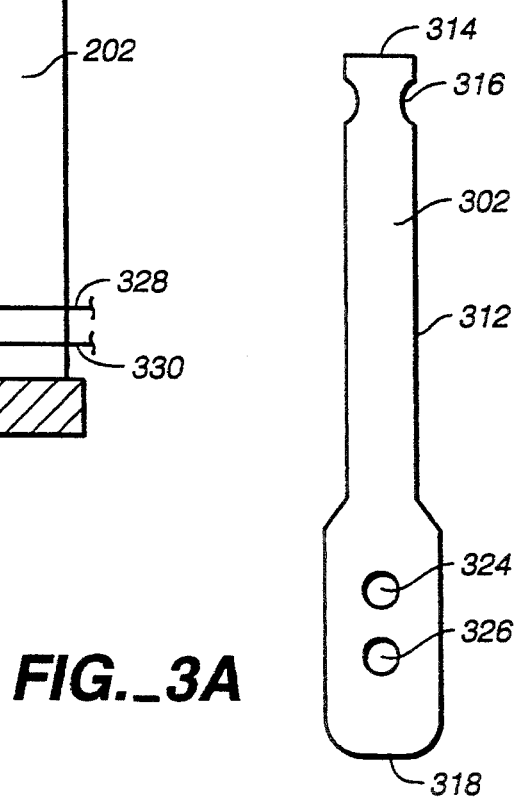
FIG._3A
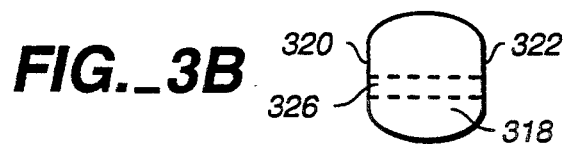
FIG._3B
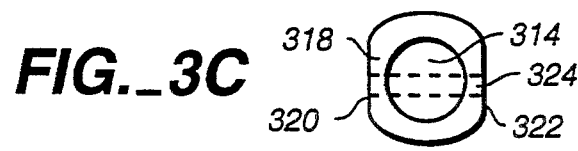
FIG._3C

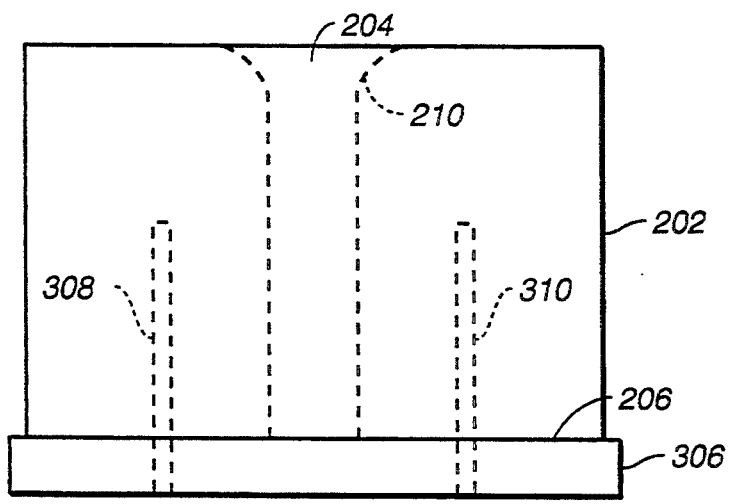
FIG._2A
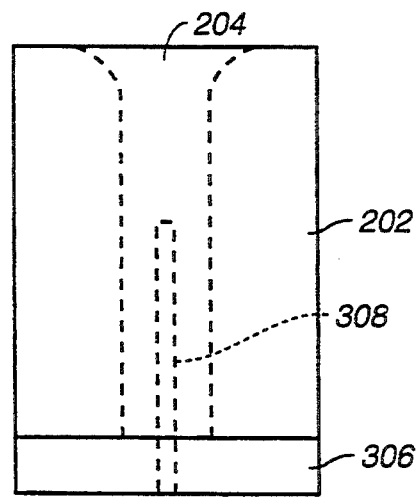
FIG._2B
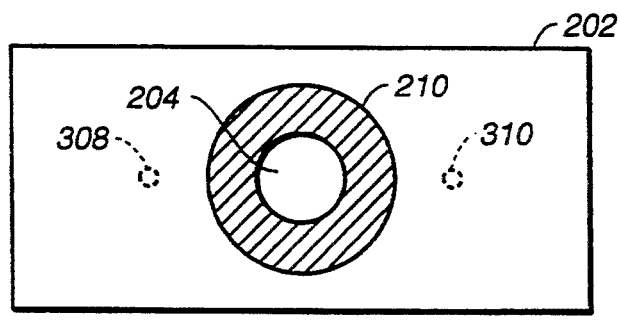
FIG._2C
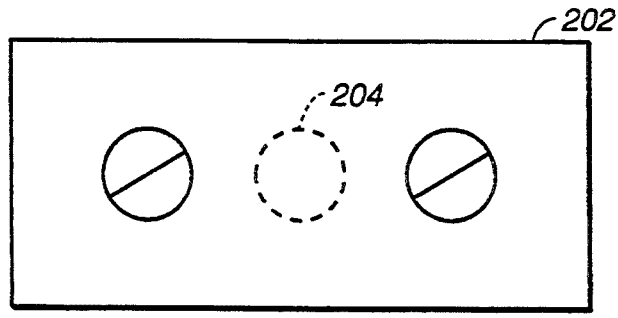
FIG._2D

METHOD AND APPARATUS FOR MEASURING RESISTIVITY OF GEOMETRICALLY UNDEFINED MATERIALS

BACKGROUND OF THE INVENTION

1. Field of the Invention

The present invention relates generally to measuring the electrical characteristics of a material, and more particularly to measuring the resistivity or conductivity of materials which do not possess a defined geometry, such as powder samples.

2. State of the Art

Techniques for measuring the conductivity of a material are well known. Conductivity corresponds to the inverse of resistivity, and these two electrical characteristics can easily be correlated to one another.

Typically, the conductivity of a material is measured by contacting two probes (e.g., the probes of a conventional ohmmeter) to opposite ends of the material. A constant electrical current is passed via the two probes through the material. By measuring this current for a given voltage across the two probes, the resistance, and thus the conductivity, of the material can be determined.

The foregoing measurement technique is relatively accurate for detecting conductivity of solid materials having a relatively well defined geometry. However, such a measurement is relatively inaccurate for measuring the conductivity of materials which do not have well defined geometries, such as powders and other compressible materials. One reason for the inaccuracy of this measurement is an inability to establish reproducible contact between the probes and the material.

Accordingly, there is a need for an apparatus and method which can accurately detect electrical characteristics such as conductivity of materials which do not possess well defined geometries.

SUMMARY OF THE INVENTION

The present invention relates to an apparatus and method for measuring electrical characteristics of materials having undefined geometries in an accurate and reproducible manner. Generally speaking, electrical characteristics such as conductivity and resistance are measured by compressing the material with a predetermined pressure in a controlled manner to provide reproducible results. As referenced herein, the term "conductivity" is considered to encompass any measurement which can be correlated to a material's ability to conduct an electric charge, including resistance and resistivity measurements.

In an exemplary embodiment, the invention relates to an apparatus which includes means for receiving a material, and means for measuring conductivity of the material in the receiving means. The conductivity measuring means includes means for applying pressure to said material during said conductivity measurement.

Further, the invention relates to a method for measuring electrical characteristics of a material. In an exemplary embodiment, the method includes the steps of placing said material into a receptacle and measuring conductivity of the material placed into said receptacle by applying pressure to the material during said conductivity measurement.

BRIEF DESCRIPTION OF THE DRAWINGS

FIG. 1 shows an exemplary apparatus for measuring electrical characteristics of a geometrically undefined material in accordance with the present invention;

FIGS. 2a–2d show an exemplary receiving means for use in accordance with the present invention; and FIGS. 3a–3c show an exemplary probe for use with the measuring means illustrated in FIGS. 2a–2d.

DETAILED DESCRIPTION OF THE PREFERRED EMBODIMENTS

FIG. 1 shows an apparatus 100 for providing accurate, reproducible measurements of electrical characteristics of a geometrically undefined material. For purposes of the following discussion, specific reference will be made to measuring the electrical characteristics of a conductive powder material. Exemplary powders which can be accurately measured in accordance with the present invention include carbon (e.g., graphite or acetylene black). However, those skilled in the art will appreciate that characteristics of any powder can be measured (e.g., nickel, copper, zinc or metal oxide powders, or any combination thereof) as well as any other material of relatively unpredictable geometry.

The FIG. 1 apparatus 100 includes a material receiving means 200 and a conductivity measuring means 300. The material receiving means includes a non-conductive block 202 formed with a receptacle 204 for receiving material whose electrical characteristics are to be measured. The conductivity measuring means includes a pressure plate 306 attached at a first end 206 of the non-conductive block. The pressure plate 306 thus covers the receptacle which passes through the non-conductive block.

The conductivity measuring means 300 further includes a probe 302 which can be inserted into the receptacle 204 from a second end of the non-conductive block, the second end 208 being opposite the first end 206. The probe 302 compresses any material placed within the receptacle 204 against the pressure plate 306.

The material receiving means is illustrated in greater detail in FIGS. 2a–2d. FIG. 2a is a front view of the material receiving means, FIG. 2b is a side view of the material receiving means (both sides being substantially identical), and FIG. 2c is a top view of the material receiving means. FIG. 2d shows a bottom view of the non-conductive block with the pressure plate 306 of the measuring means secured in place.

The non-conductive block 202 is formed of an insulator material, such as plastic. However, those skilled in the art will appreciate that any insulating material can be used to form the nonconductive block 202. In an exemplary embodiment, the plastic is transparent to permit visual inspection of an interior portion of the receptacle 204.

The receptacle 204 is formed, for example, as a cylindrical hole through the non-conductive block 202. As best illustrated in FIG. 2c, the cylindrical hole is centrally located on a top surface (i.e., the second end) of the non-conductive block 202. Viewing the non-conductive block 202 from the top, the opening of the cylindrical hole at the second end of the receptacle 204 is formed with an increased diameter that tapers inward to a reduced diameter. This forms a tapered portion 210 that slopes inward with a relatively constant slope. The tapered portion of the receptacle assists in receiving the FIG. 1 probe 302 of the conductivity measuring means.

The receptacle is of circular cross-section with relatively constant diameter between a lower end of the tapered portion 210 and the first end 206 of the non-conductive block.

In an exemplary embodiment, the pressure plate 306 of the conductivity measuring means is attached to the first end of the non-conductive block 202. The pressure plate can be integrally formed with the non-conductive block 202. However, where the pressure plate is used as a conductive probe, it can be attached to the non-conductive block by any suitable means. As shown in FIG. 2a, the pressure plate 306 can, for example, be formed of copper and attached to the first end 206 of the non-conductive block 202 using two screws for insertion through the pressure plate and into threaded screw holes 308 and 310 of the non-conductive block.

Exemplary dimensions of the non-conductive block 202 are approximately $2\frac{3}{8}$" long by 1" wide. The height of the block is approximately 1". The diameter of the cylindrical borehole which forms the receptacle 204 is approximately $\frac{1}{2}$", but as described above, tapers to a wider opening of approximately $\frac{5}{8}$" at the second end (i.e., top) of the block. The threaded screw holes for receiving screws to attach a pressure plate extend approximately $\frac{3}{4}$" into the block from the first end 206. The threaded screw holes are symmetrically located on either side of the receptacle 204, approximately $\frac{1}{2}$" away from an axis through the center of the receptacle.

The pressure plate is attached to the first end 206 (i.e., bottom) of the block 202 and has a length and width which approximately correspond to that of the block. A height of the pressure plate is approximately $\frac{1}{4}$". Holes through the pressure plate correspond to the threaded screw holes in the block so that screws for attaching the pressure plate to the block can be inserted therein. The screws are shown in place in FIG. 2d.

An exemplary probe 302 for use with the conductivity measuring means of FIG. 1 is illustrated in greater detail in FIGS. 3a–3c. As shown in FIG. 3a, the probe is formed with a shaft that is shaped to match the receptacle 204 of the material receiving means for insertion therein. In an exemplary embodiment, the probe 302 is formed with a cylindrically shaped shaft 312 of slightly less diameter than the cylindrically shaped receptacle 204. Those skilled in the art will appreciate that other shapes, such as square, octagonal and so forth, can be used for the cylindrically shaped probe shaft 312 and receptacle 204 provided a suitable tolerance (e.g., 0.004 inch tolerance) can be observed in matching the outer probe diameter to the inner receptacle diameter.

The probe 302 is formed with a relatively flat probe tip 314. The probe tip 314 is inserted into the receptacle 204 and thus faces the pressure plate 306 when the probe is inserted into the receptacle. The probe tip 314 of the probe 302 can be used to compress material placed within the receptacle against the pressure plate 306.

In accordance with a significant feature of the invention, the probe 302 further includes a means for removing excessive material from a measurement area of the receptacle 204. The measurement area corresponds to an area within the receptacle between the probe tip 314 and the pressure plate 306 where compressed material resides during a measurement. An exemplary embodiment of the means for removing excess material is formed (e.g., machined) as a groove 316 having a semi-circular cross-section along a length of the probe shaft. The groove 316 is formed on the probe 302, just above the probe tip 314. The groove 316 is formed about a periphery of the probe such that the material which escapes from the measurement area during movement of the probe 302 will not cause the probe to jam in the receptacle when the material is compressed in response to a predetermined force.

A probe end 318 which is opposite the probe tip 314 is not inserted into the receptacle 204 and can be formed in any suitable manner for applying pressure to the probe. The probe end 318 can have a diameter greater than that of the receptacle 204. In an exemplary embodiment, the probe end 318 is generally cylindrical in shape with two flat machined sides 320, 322. The probe end 318 can be operatively connected with a pressure generating means, such as any conventional press (e.g., hydraulic, pneumatic and so forth).

Where the probe 302 is used as an electrical probe for performing a conductivity measurement, the probe is formed of conductive material (e.g., copper) and two contact holes 324, 326 are formed through the probe end 318. Current supply/measurement contacts are inserted into the contact holes 324, 326 for supplying current to the probe 302 and for performing a current and/or voltage measurement of material in the measurement area.

An exemplary probe for use in connection with the present application is approximately $2\frac{3}{4}$" long. A diameter of the probe at its probe tip 314 complies with the aforementioned tolerance (i.e., within 0.004" or less) relative to the diameter of the receptacle 204 in the block 202. The probe end 318 of the probe which connects to, for example, a hydraulic press, can taper outward to a diameter which exceeds that of the probe tip 314 and the receptacle 204. The groove 316 formed near the probe tip 314 can be formed approximately $\frac{1}{8}$" from the probe tip 314, and can be shaped with a semi-circular cross-section having a radius (i.e., indentation relative to the outer diameter of the probe) of approximately 1/16" for the exemplary probe described herein.

In operation, a two probe conductivity or resistivity measurement of a material can be performed using the FIG. 1 apparatus. A two probe conductivity measurement refers to the use of two probes to measure both current (I) through the material and the voltage (V) across the material. Where the probe 302 and pressure plate 306 are formed of a conductive material (e.g., copper), a fixed current can be applied to the probe 302 by connecting current supply contacts to the contact holes 324, 326. Further, current detection contacts can be connected with the pressure plate 306.

The current supply and current detection contacts can be connected at their opposite ends to, for example, an ohmmeter. By applying a known voltage from the probe 302 across the material compressed in the measuring area and into the pressure plate 306, a current through the measuring area can be determined. Using the voltage and current values, a conductivity and/or resistivity measurement can be provided.

In an alternate embodiment, a four probe conductivity and/or resistivity measurement can be performed by integrally forming at least one contact in the material receiving means. In an exemplary embodiment as illustrated in FIG. 1, two such contacts 328 and 330 are formed in the material receiving means. For example, the contacts 328 and 330 can be formed as metal sheets sandwiched (e.g., laminated) between three plastic blocks using any conventional techniques. Of significance is that the metal sheets are exposed within the receptacle 204 for communicating with an interior of said receptacle and for contacting material compressed therein, and that opposite ends of the metal sheets are exposed on an exterior of the FIG. 1 apparatus for connection with a voltmeter or ohmmeter.

Because the metal sheets are used to perform a voltage measurement, the exposed ends of these sheets which contact the material in the measurement area should be as small as is practical. The small area does not detrimentally affect the accuracy of the measurement because the current that flows through the contact area is very small (e.g., in the microamp to nanoamp range). However, the use of thin metal sheets as the contacts 328 and 330 permits the distance between the metal sheets to be determined with enhanced accuracy for purposes of providing a voltage measurement. As the thickness of the sheets is increased, it becomes increasingly difficult to accurately determine their separation distance.

Although the probe 302 and pressure plate 306 can be used to perform both a current measurement and a voltage measurement of the compressed material, resistance at the contact between the material and the probe 302 or the pressure plate 306, as well as resistance at the current supply contacts of the probe 302 and pressure plate 306, can detrimentally affect the voltage measurement. In accordance with the alternate embodiment described herein, the contacts 328 and 330 are separated by a known distance and can be used to perform a separate voltage measurement across the contacts 328 and 330 (i.e., from the contact 328 to the contact 330). This measurement is not affected by the contact resistance which may exist between contact probe 302 or the pressure plate 306 and the material in the measurement area.

The integrally formed contacts 328 and 330 can be formed in the measurement area with minimal contact resistance between the metal sheets and the material. In this embodiment, the contacts 328 and 330 can be used to perform a voltage measurement while constant current is passed from the probe 302 to the pressure plate 306. The result is a true 4 probe measurement of conductivity and/or resistivity (i.e., resistance per unit length and unit cross-sectional area).

A method for performing a two or four probe measurement in accordance with the present invention can be implemented as follows. A predetermined amount (e.g., a known weight) of material to be considered is placed into the receptacle 204.

Using an exemplary embodiment, a resistivity measurement of cathode powder was performed. The probe had a diameter of 0.420" (i.e., 1.0867 cm), corresponding to a cross-sectional area of 0.894 cm². A portion of the cathode powder was weighed at 1.045 g at normal atmospheric pressure.

The sample of cathode powder was placed into the receptacle of the non-conductive block. The probe was then inserted into the receptacle and pressed using a hydraulic press pressurized with a predetermined pressure or force (e.g., force due to 400 kg mass). A conductivity measuring step can then be repeated at various times and pressures to ensure that a conductivity measurement remains within a predetermined range of variation (i.e., tolerance) specified by the operator (e.g., plus or minus 0.001 ohms).

For example, maintaining a constant force due to a 400 kg mass, a resistance measurement was performed in the exemplary embodiment mentioned above at time intervals of one minute, five minutes and ten minutes, resulting in a resistance of 0.122 ohms, 0.121 ohms and 0.122 ohms, respectively. The measurement was performed using a four wire ohm setting of a Hewlett-Packard Multimeter, such as the HP Model 3468A, available from Hewlett-Packard Company.

When inserted, the top of the probe relative to the bottom of the pressure plate was 3.032". Upon releasing the predetermined force from the probe, the resistance measurement was 0,581 ohms. This pressure release step was performed by retracting the probe from the receptacle in the non-conductive block to a position where the top of the probe was 3.248" above the surface upon which the bottom of the pressure plate was resting. Afterwards, the predetermined force was reapplied at 400 kg and resulted in a resistance reading of 0.121 ohms. Upon subsequently increasing pressure to a second predetermined force of twice the original force (i.e., force due to 800 kg mass), a reading of 0.121 ohms was again obtained. Thus, the thickness of the sample was determined to be 0.196" (or 0.498 cm). A resistance of the sample, measured at 0.122 ohms, multiplied by 1/0.498 cm and multiplied by 0.894 cm² (i.e., approximate circular cross-sectional area of the probe shaft 312 and of the sample in the cylindrically shaped receptacle) correlates to a resistivity of 0.218 ohms per centimeter.

Those skilled in the art will appreciate that many other embodiments of an apparatus for measuring electrical characteristics of a material in accordance with the present invention can be constructed. For example, a pressure plate can be used which is separate from the conductive plate used for measuring electrical characteristics of the material. In this case, a conductive (e.g., copper) plate can be attached to the bottom of the non-conductive block as a probe for performing the conductivity measurement, and this copper plate can be attached on its bottom to an aluminum plate such that the copper plate and the aluminum plate are sandwiched between the non-conductive block and a pressure plate attached to an opposite side of the aluminum plate. Further, by including ceramic plate insulation between the pressure plate and a frame upon which the measurement apparatus is resting, the possibility of short-circuits from a top pressure plate which acts on the probe end 318 to the bottom pressure plate through the frame can be avoided.

It will be appreciated by those skilled in the art that the present invention can be embodied in other specific forms without departing from the spirit or essential characteristics thereof. The presently disclosed embodiments are therefore considered in all respects to be illustrative and not restricted. The scope of the invention is indicated by the appended claims rather than the foregoing description and all changes that come within the meaning and range and equivalence thereof are intended to be embraced therein.

What is claimed is:

1. Apparatus for measuring electrical characteristics of a material comprising:
   means for receiving said material, said material receiving means including a cylindrically-shaped receptacle and two conductive sheets integrally formed in said receiving means in contact with said receptacle for providing a first electrical measurement of said material; and
   conductivity measuring means for measuring a conductivity measurement of said material placed in said receiving means, said conductivity measuring means including means for applying pressure to said material during said conductivity measurement.

2. Apparatus according to claim 1 wherein said receiving means further includes:
a non-conductive block formed with said receptacle for receiving said material and for receiving said pressure applying means.

3. Apparatus according to claim 2, wherein the non-conductive block is formed of transparent plastic with said cylindrically shaped receptacle formed therein.

4. Apparatus according to claim 3, wherein said conductivity measuring means further includes:
a pressure plate attached at a first end of said non-conductive block.

5. Apparatus according to claim 4, wherein said pressure applying means includes:
a probe for insertion into said receptacle from a second end of said non-conductive block, said second end being opposite said first end such that said probe compresses material placed in said receptacle against said pressure plate.

6. Apparatus according to claim 5, wherein said pressure plate and said probe are formed of conductive metal material, said conductive probe further including:
a relatively flat tip which faces said pressure plate when said probe is inserted into said receptacle, such that said conductivity measuring means measures conductivity of material compressed between said pressure plate and said relatively flat tip of said probe to provide a two probe measurement using said probe and said pressure plate.

7. Apparatus according to claim 1, wherein said pressure applying means includes:
a probe for insertion into said material receiving means to compress said material with a predetermined pressure.

8. Apparatus according to claim 7, wherein said probe is cylindrically shaped, and further includes:
means for removing excess material from a measurement area of said material receiving means during compression of said material.

9. Apparatus according to claim 8, wherein said removing means is formed as a groove about a periphery of said probe.

10. Apparatus according to claim 9, wherein said conductivity measuring means further includes:
a pressure plate attached at a first end of said receptacle,
said probe having a relatively flat tip which faces said pressure plate when said probe is inserted into said receptacle, said conductivity measuring means measuring conductivity of material compressed between said pressure plate and said relatively flat tip of said probe to provide a two probe measurement using said probe and said pressure plate.

11. Apparatus according to claim 1, further including:
a pressure plate attached at a first end of said receptacle; and
a probe with a relatively flat tip which faces said pressure plate when said probe is inserted into said receptacle such that said conductivity measuring means measures conductivity of material compressed between said pressure plate and said relatively flat tip of said probe to provide a two probe measurement using said probe and said pressure plate.

12. Apparatus according to claim 11, wherein said pressure plate and said probe are conductive.

13. Apparatus according to claim 1, wherein said material is a powder.

14. Method for measuring electrical characteristics of a material comprising the steps of:
placing said material into a cylindrically-shaped receptacle, said cylindrically-shaped receptacle further including two conductive sheets integrally formed in contact with said cylindrically-shaped receptacle for providing a first conductivity measurement of said material;
performing a second conductivity measurement using a probe inserted into said receptacle; and
measuring conductivity of the material placed into said receptacle by applying pressure to the material during said first and second conductivity measurements.

15. Method according to claim 14, wherein said measuring step further includes a step of:
inserting said probe into said receptacle to compress said material with a predetermined force.

16. Method according to claim 15, wherein said measuring step further includes a step of:
applying current to said probe to measure conductivity of said compressed material.

17. Method according to claim 15, wherein said measuring step further includes a step of:
applying current to said probe to perform a first measurement of said compressed material; and
performing a voltage measurement within said receptacle using said two conductive sheets.

18. Method according to claim 15, further comprising a step of:
repeating said conductivity measuring step until a conductivity measurement remains within a predetermined range of variation.

19. A method according to claim 15, wherein said material is a conductive powder.

20. Apparatus for measuring electrical characteristics of a material comprising:
means for receiving said material; and
means for measuring conductivity of said material placed in said receiving means, said conductivity measuring means including means for applying pressure to said material during said conductivity measurement, said pressure applying means including a probe for insertion into said material receiving means to compress said material, said probe including a groove formed on a periphery thereof for removing excess material from a measurement area of said material receiving means during compression of said material.

21. Apparatus according to claim 20 wherein said receiving means includes:
a non-conductive block with a cylindrically shaped receptacle for receiving said material and for receiving said probe, the non-conductive block being formed of transparent plastic with said cylindrically shaped receptacle formed therein.

22. Apparatus according to claim 21, wherein conductivity measuring means further includes:
a pressure plate attached at a first end of said non-conductive block, said probe being inserted into said receptacle from a second end of said non-conductive block, said second end being opposite said first end such that said probe compresses material placed in said receptacle against said pressure plate.

23. Apparatus according to claim 22, wherein said pressure plate and said probe are formed of conductive metal material, said conductive probe further including:

a relatively flat tip which faces said pressure plate when said probe is inserted into said receptacle, such that said conductivity measuring means measures conductivity of material compressed between said pressure plate and said relatively flat tip of said probe to provide a two probe measurement.

24. Apparatus according to claim 23, wherein said groove has a semi-circular cross-section formed about a periphery of said probe.

25. Apparatus according to claim 20, wherein said receiving means further includes:

a receptacle for receiving said material; and at least one conductive sheet integrally formed in said receiving means for communicating with said receptacle.

26. Apparatus according to claim 25, further including:

a pressure plate attached at a first end of said receptacle, said probe having a relatively flat tip which faces said pressure plate when said probe is inserted into said receptacle such that said conductivity measuring means measures conductivity of material compressed between said pressure plate and said relatively flat tip of said probe to provide a two probe measurement using said probe and said pressure plate.

27. Apparatus according to claim 26, wherein said pressure plate and said probe are conductive, and said receiving means includes:

two conductive sheets integrally formed in said receiving means in contact with said receptacle for providing a voltage measurement of said material.

28. Apparatus according to claim 27, wherein said two conductive sheets are separated by a known distance to reduce contact resistance with respect to material being measured.

* * * * *